US012752120B2

(12) United States Patent
Luther et al.

(10) Patent No.: US 12,752,120 B2
(45) Date of Patent: Oct. 6, 2026

(54) APPARATUS FOR TERMINATING CARDIAC ARRHYTHMIAS BY DECELERATION PACING

(71) Applicant: Max-Planck-Gesellschaft zur Förderung der Wissenschaften e.V., Munich (DE)

(72) Inventors: Stefan Luther, Göttingen (DE); Ulrich Parlitz, Gleichen (DE); Thomas Lilienkamp, Nuremberg (DE)

(73) Assignee: Max-Planck-Gesellschaft zur Förderung der Wissenschaften e.V., Berlin (DE)

( * ) Notice: Subject to any disclaimer, the term of this patent is extended or adjusted under 35 U.S.C. 154(b) by 58 days.

(21) Appl. No.: 18/927,329

(22) Filed: Oct. 25, 2024

(65) Prior Publication Data

US 2025/0041609 A1 Feb. 6, 2025

Related U.S. Application Data

(63) Continuation-in-part of application No. PCT/EP2023/060994, filed on Apr. 26, 2023.

(30) Foreign Application Priority Data

Apr. 27, 2022 (EP) .................................... 22170378

(51) Int. Cl.

*A61N 1/365* (2006.01)
*A61N 1/37* (2006.01)
*A61N 1/39* (2006.01)

(52) U.S. Cl.

CPC ........... *A61N 1/365* (2013.01); *A61N 1/3702* (2013.01); *A61N 1/3906* (2013.01); *A61N 1/3925* (2013.01)

(58) Field of Classification Search

CPC ..... A61N 1/365; A61N 1/3702; A61N 1/3925

See application file for complete search history.

(56) References Cited

U.S. PATENT DOCUMENTS

| | | | |
|---|---|---|---|
| 5,702,424 | A | 12/1997 | Legay et al. |
| 6,317,632 | B1 | 11/2001 | Krig et al. |
| 7,113,824 | B2 | 9/2006 | Krig et al. |
| 7,522,956 | B2 | 4/2009 | Krig et al. |
| 8,046,068 | B2 | 10/2011 | Krig et al. |
| 8,306,619 | B2 | 11/2012 | Krig et al. |
| 8,886,309 | B2 | 11/2014 | Luther et al. |
| 9,289,618 | B1 | 3/2016 | Ben-Haim et al. |
| 9,855,439 | B2 | 1/2018 | Krinski et al. |
| 10,870,006 | B2 | 12/2020 | Schlemmer et al. |

(Continued)

FOREIGN PATENT DOCUMENTS

| | | |
|---|---|---|
| JP | H 09-117517 A | 5/1997 |
| JP | 2020-503094 A | 1/2020 |

(Continued)

*Primary Examiner* — Rochelle D Turchen

(74) *Attorney, Agent, or Firm* — Thomas | Horstemeyer, LLP

(57) ABSTRACT

An apparatus for determining an arrhythmia of a living heart comprises a signal evaluation device receiving a signal representing a present electric activity of the heart, and determining a frequency spectrum of the signal. The apparatus further comprises a pulse generator generating a sequence of electric pulses to be applied to the heart at a pulse repetition frequency that depends on the frequency spectrum and decreases by at least 20% over the sequence.

20 Claims, 12 Drawing Sheets

(56) References Cited

U.S. PATENT DOCUMENTS

| | | | |
|---|---|---|---|
| 11,167,144 | B2 | 11/2021 | Woerden et al. |
| 2013/0046194 | A1 | 2/2013 | Bjolring et al. |

FOREIGN PATENT DOCUMENTS

| | | | |
|---|---|---|---|
| WO | WO2011134499 | A1 | 11/2011 |
| WO | WO2012172027 | A2 | 12/2012 |
| WO | WO2017157954 | A1 | 9/2017 |

APPARATUS FOR TERMINATING CARDIAC ARRHYTHMIAS BY DECELERATION PACING

CROSS REFERENCE TO RELATED APPLICATIONS

This application is a continuation in part of International Application No. PCT/EP2023/060994 entitled "Apparatus for terminating cardiac arrhythmias by deceleration pacing" filed on Apr. 26, 2023 and claiming priority to European Patent Application No. EP 22 170 378.8 also entitled "Apparatus for terminating cardiac arrhythmias by deceleration pacing" and filed on Apr. 27, 2022, the disclosures of which are hereby incorporated herein by reference in their entirety.

FIELD OF THE INVENTION

The invention relates to an apparatus for terminating an arrhythmia of a living heart.

In the present description and the accompanying claims, the term 'arrhythmia of a living heart' refers to all kinds of cardiac arrhythmias, particularly including ventricular and atrial fibrillation. Cardiac arrhythmias are the major cause of morbidity and mortality with sudden cardiac death taking several hundreds of thousands of lives per year. The complex and chaotic dynamics of the underlying electrical excitation patterns in the heart are still not fully understood. However, it is known that spiral or scroll waves are the governing objects which drive the spatial-temporal dynamics during arrhythmias.

BACKGROUND OF THE INVENTION

The conventional treatment of ventricular fibrillation consists of applying an electrical defibrillation pulse, aiming to restore sinus rhythm. Due to the significant electrical current induced in the heart, this treatment comes along with severe side-effects, including tissue damage and posttraumatic stress.

International application publication WO 2012/172 027 A2 and United States patent U.S. Pat. No. 8,886,309 belonging to the same patent family disclose an apparatus for terminating a high frequency arrhythmic electric state of a biological tissue. The apparatus comprises a sensor for providing an electric signal representative of the present electric state of the biological tissue. A determination unit determines a dominant frequency of the present electric state of the biological tissue from the electric signal, and whether the present electric state of the biological tissue is a high frequency arrhythmic electric state from the dominant frequency. Particularly, the determination unit determines that the biological tissue is in a high frequency arrhythmic electric state, if the dominant frequency is in a frequency range from 5 Hz to 20 Hz. Further, the determination unit determines a dominance level indicative of how dominant the at least one dominant frequency is in the high frequency arrhythmic electric state, and triggers an electric pulse generator to generate a series of electric pulses at intervals depending on the dominant frequency at a point in time at which the dominance level exceeds a predefined threshold value. The electric pulse generator generates the electric pulses of the series at such intervals and in such a number that the electric pulses raster scan a phase space defined by the dominant frequency once. Particularly, the electric pulses generator generates electric pulses at such intervals that the electric pulses raster scan the phase space at phase intervals in a range from $\pi/5$ to $2\pi/7$. Even more particularly, the pulse generator generates electric pulses at intervals exceeding the reciprocal value of the dominant frequency by 1/10 to 1/7 of the reciprocal value of the dominant frequency. Using the known apparatus the application of electric pulses at an electric energy per pulse in a range of 1/100 to 1/10 of a standard heart defibrillation energy can be sufficient for terminating the high frequency arrhythmic electric state of the biological tissue. In other words, the electric pulse generator generates the electric pulses according to the so-called LEAP (Low Energy Anti-fibrillation Pacing) concept at a comparatively low electric energy as compared to a standard defibrillation energy used for defibrillation by means of a single pulse providing an electric shock. The effectiveness of the LEAP concept depends on the careful selection of an optimum starting point for applying the electric pulses to the biological tissue.

International application publication WO 2017/157 954 A1 and United States patent U.S. Pat. No. 10,870,006 belonging to the same patent family disclose an apparatus for applying at least one electric pulse to a living myocardial tissue comprising an input receiving an electric signal representing a present electric activity of the myocardial tissue. A signal processor processes the electric signal to determine a measure of the present complexity of the electric signal in the state space and to output a control signal when the complexity measure is lower than a predetermined complexity threshold value. A pulse generator generates the at least one electric pulse in response to the control signal. Via an output, the at least one electric pulse is output to the myocardial tissue. Particularly, the complexity measure is determined as a calculated present permutation entropy of the electric signal. In this way, the at least one electric pulse shall be triggered at an optimum point in time such that a desired resetting effect of the at least one electric pulse on the living myocardial tissue is achieved at an as low as possible electric energy.

There still is a need of an apparatus having an enhanced success rate in terminating an arrhythmia of a living heart.

SUMMARY OF THE INVENTION

The present invention relates to an apparatus for terminating an arrhythmia of a living heart. The apparatus comprises a signal evaluation device configured for receiving a signal representing a present electric activity of the heart, and for determining a frequency spectrum of the signal. The apparatus further comprises a pulse generator configured for generating a sequence of electric pulses to be applied to the heart at a pulse repetition frequency depending on the frequency spectrum in such a way that the pulse repetition frequency of the electric pulses decreases by at least 20% over the sequence.

The invention further relates to an apparatus for terminating an arrhythmia of a living heart. This apparatus comprises a signal evaluation device comprising stored evaluation instructions and, when executing the stored evaluation instructions, being configured for receiving a signal representing a present electric activity of the heart, and for determining a frequency spectrum of the signal. The apparatus further comprises a pulse generator comprising stored generation instructions and, when executing the stored generation instructions, being configured for generating a sequence of electric pulses to be applied to the heart at a variable pulse repetition frequency that depends on the frequency spectrum in such a way that the variable pulse repetition frequency of the electric pulses decreases by at least 20% over the sequence.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components of the drawings are not necessarily to scale, emphasize instead being placed upon clearly illustrating the principles of the present invention. In the drawings, like reference numerals designate corresponding parts throughout the several views.

DETAILED DESCRIPTION

Figure 1:
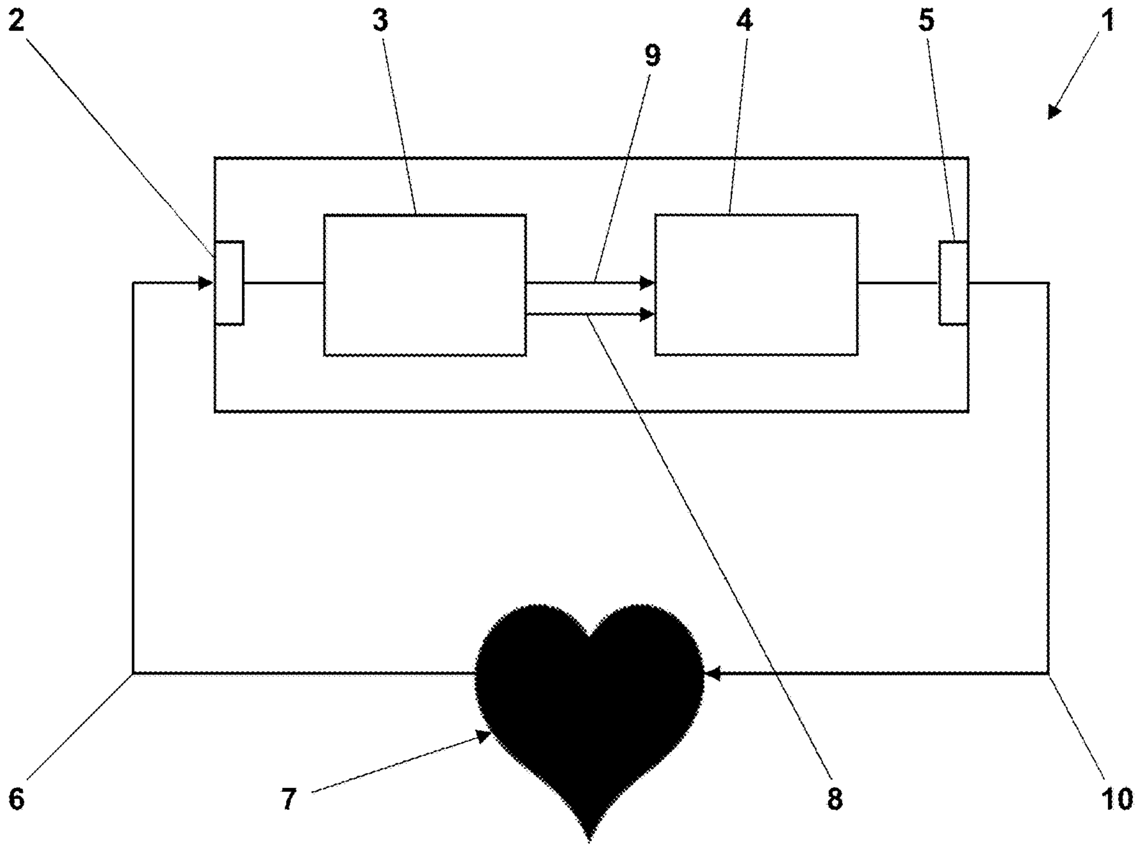
FIG. 1 schematically shows an apparatus according to the present disclosure.

An apparatus for determining an arrhythmia of a living heart according to the present disclosure comprises a signal evaluation device receiving a signal representing a present electric activity of the heart, and determining a frequency spectrum of the signal. The apparatus further comprises a pulse generator generating a sequence of electric pulses to be applied to the heart at a pulse repetition frequency depending on the frequency spectrum and decreasing by at least 20% over the sequence.

The arrhythmia may particularly be a ventricular fibrillation (VF) or an atrial fibrillation (AF). It may, for example, also be a ventricular tachycardia (VT).

The frequency spectrum may, for example, be a spectrum of an amplitude or voltage of the signal, or a spectrum of the power density of the signal, i.e. a Power-Spectral-Density (DSD).

Like most known apparatuses for determining an arrhythmia of a living heart, the apparatus according to the present disclosure may comprise a dedicated input for the signal representing the present electric activity of the heart, and a dedicated output for outputting the sequence of electric pulses to be applied to the heart.

The pulse generator of the apparatus according to the present disclosure does not generate the pulses of the sequence of electric pulses at a fixed pulse repetition frequency, i.e. at fixed intervals in time. Instead, the pulse repetition frequency is lowered over the sequence of electric pulses, i.e. the electric pulses are generated at intervals in time which increase by at least 25% over their sequence. This concept is called ‘deceleration pacing’.

In extensive research, the inventors of the present disclosure found sweet spots in which arrhythmias of a living heart can be terminated with a sequence of electric pulses of a constant pulse repetition frequency at a comparatively low electric energy per pulse. Some of these sweet spots are delimited by areas of reduced efficiency of the electric pulses not only in the direction of even lower electric energy per pulse, but also in the direction of higher electric energy per pulse. With the broad variance of real living hearts, these sweet spots are hard to find in practice. At least, it would take too much time to find them. Thus, the inventors thought about a way of making use of the high efficiency of the electric pulses in such a sweet spot without having to actually find the sweet spot. One attempt was to use a frequency sweep such as to include the pulse repetition frequency of the sweet spot in the sequence of electric pulses at least in some way. In their experiments, the inventors found that a sweep with decreasing pulse repetition frequency provides much better results than a sweep with increasing pulse repetition frequency. Further, they found criteria by which the course of the pulse repetition frequency can be optimized. This optimization goes far beyond a simple frequency sweep aiming at including the pulse repetition frequency of an unknown sweet spot at least in some way.

The pulse repetition frequency may start above a present dominant frequency of the signal representing the present electric activity of the heart; and the pulse repetition frequency may drop far below the present dominant frequency. However, the signal evaluation device of the apparatus according to the present disclosure does not need to determine any dominant frequency of the signal. Instead, other criteria may be applied in setting the course of the pulse repetition frequency over the sequence of the electric pulses. These other criteria are more robust than the dominant frequency, and they do not even require a signal having any dominant frequency which could be determined.

Generally, the pulse generator of the apparatus according to the present disclosure generates the sequence of the electric pulses such that their pulse repetition frequency decreases monotonically or even strictly monotonically. In a strictly monotonic decrease of the pulse repetition frequency the distance in time between two consecutive electric pulses will increase pulse by pulse.

Very often, the pulse generator of the apparatus according to the present disclosure will generate the sequence of the electric pulses such that the pulse repetition frequency of the electric pulses decreases by at least 30% of its start value over the sequence. This means that the intervals in time at which the electric pulses are generated increase by more than 40% of their start value over the sequence. Often, the pulse repetition frequency of the electric pulses will decrease by at least 50% of its start value over the sequence, so that the intervals in time at which subsequent electric pulses follow to each other increase by at least 100% of their start value.

Very often the decrease of the pulse repetition frequency over the sequence will be not more than 80%, and often it will be not more than 70% of its start value. This corresponds to an increase of the intervals of the electric pulses by 500% and 333% of their start value, respectively.

The pulse generator of the apparatus according to the present disclosure may generate at least 3 or 4 electric pulses per sequence. A maximum number of the electric pulses per sequence may be 20 or 15. Thus, the number of electric pulses will often be in a range from 4 to 15.

The pulse repetition frequency may begin with a fixed start value, and the decrease of the pulse repetition frequency may be linearly distributed over the sequence of the electric pulses. However, the inventors found that there are even better options for setting the start value and distributing the decrease. These options will be explained in the following:

The pulse generator may generate the sequence of the electric pulses such that a high frequency part of an integral of the frequency spectrum down to a start value of the pulse repetition frequency of the electric pulses of the sequence is at least 5% or at least 8%, and not more than 25% or not more than 20% or even not more than 15%, of the full integral of the frequency spectrum. The integral of the frequency spectrum is a suitable reference of the apparatus according to the present disclosure in setting the pulse repetition frequency of the electric pulses of the sequence. This integral may be limited to frequencies, i.e. only calculated for frequencies, up to a maximum frequency relevant for an arrhythmia of the living heart. This upper cut-off frequency may, for example, be set to 20 Hz or 15 Hz or 10 Hz or even less, or to that frequency at which the signal clearly exceeds a background noise. With regard to ventricular tachycardia, the upper cut-off may be set such that the harmonics of a dominant frequency of the tachycardia are not in the integral. Thus, the upper cut-off may be set between the dominant frequency and twice the dominant frequency. Similarly, the integral may be limited to frequencies, i.e. only calculated for frequencies, above a minimum frequency relevant for the arrhythmia of the living heart. This lower cut-off frequency may, for example, be set to 0.5 Hz or 1 Hz or even more. The start value of the pulse repetition frequency set using the integral as defined above is clearly within the frequency spectrum of the signal representing the present electric activity of the heart in an arrhythmia, but close to the upper end of this frequency spectrum. In absolute terms, the start value of the pulse repetition frequency of the electric pulses of the sequence may be at least 5 Hz or at least 8 Hz, and not more than 15 Hz, or not more than 10 Hz. Typically, the start value of the pulse repetition frequency will be lower when determined based on a PSD rather than on an amplitude frequency spectrum.

Further, the pulse generator of the apparatus according to the present disclosure may generate the sequence of the electric pulses such that a low frequency part of the integral of the frequency spectrum up to an end value of the pulse repetition frequency of the electric pulses of the sequence is at least 5% or at least 8%, and not more than 25% or not more than 20% or even not more than 15%, of the full integral of the frequency spectrum. In absolute terms the end value of the pulse repetition frequency of the electric pulses may be at least 0.5 Hz at least 2 Hz, and not more than 6 Hz or not more than 4 Hz. Thus, the deceleration pacing may be interpreted as collecting the heart at the different frequencies of its electric activity present in arrhythmia and guiding the heart towards the typical frequency of its sinusoidal electric activity which is in the range of 1 Hz to 2 Hz.

The apparatus according to the present disclosure is most successful in terminating arrhythmias at a low electric energy of the electric pulses applied, if the pulse generator generates the sequence of the electric pulses such that intermediate values of the pulse repetition frequency of the electric pulses of the sequence are arranged such as to divide the integral of the frequency spectrum into essentially equal parts or even into equal parts within the limits of the temporal variation of the frequency spectrum. In this way, the density of the intermediate values of the pulse repetition frequency is the higher the stronger the electric activity of the heart is in the respective frequency range. Stronger electric activity means that a higher effort may be required for collecting the heart at the respective frequency prior to being able to guide it towards the regular sinusoidal electric activity. In fact, the results, i.e. the arrhythmia termination rates, achieved with the apparatus generating the electric pulses according to the above scheme are equal to best matches of a start value and an end value with linearly distributed intermediate values of the pulse repetition frequency for all arrhythmias modelled in testing the present application. The best matches, however, can only be found by extensive testing, whereas the above scheme can be directly applied without testing and in or close to real time as soon as the signal representing the present electrical activity of the heart is available.

For example, the signal evaluation device may receive an ECG-signal as the signal representing the electric activity of the heart and determine the frequency spectrum of the ECG signal.

In determining the frequency spectrum of the signal representing the electric activity of the heart, the signal evaluation device may Fourier-transform the signal. This may be accomplished by a fast Fourier-transformation or by any other computer-implemented Fourier-transformation executable in or close to real time. The signal may be Fourier-transformed for a floating time window whose length may be in a typically range of 1 to 10 s.

In determining the frequency spectrum of the signal on which the pulse repetition frequency of the electric pulses is depending, the signal evaluation device may average preliminary frequency spectra or smooth a preliminary frequency spectrum of the signal representing the electric activity of the heart. In other words, for setting the pulse repetition frequency based on the integral of the frequency spectrum, the averaged or smoothed preliminary frequency spectrum is used as it will provide for a smoother course of the integral. Alternatively, the integral could be smoothed.

The pulse generator of the apparatus according to the present disclosure may generate the electric pulses of the sequence at equal voltage and energy of the pulses. Generally, however, the voltage and energy of the pulses may be varied, particularly lowered, over the sequence. In absolute terms, the voltage and energy of each of the electric pulses may be in the typical range of LEAP, i.e. in the range of 1/10 to 1/100 of the energy of a standard single electric defibrillation pulse. The shape of the electric pulses may be equal or similar to a typical electric defibrillation pulse, and the electric pulses may be applied to the heart in a same way as a typical electric defibrillation pulse.

It is to be understood, that setting the course of the pulse repetition rate of the electric pulses of the sequence according to the present disclosure does not replace the concept of applying the sequence of the electric pulses at an optimum point in time. Although the arrhythmia termination success rate of the sequence of the electric pulses with the decreasing pulse repetition rate set according to the present disclosure may be less dependent on being applied at the optimum point in time, the present disclosure may be combined with the concept of applying the sequence of the electric pulses at an optimum point in time.

Referring now in greater detail to the drawings, an apparatus 1 schematically depicted in FIG. 1 comprises an input 2, a signal evaluation device 3, a pulse generator 4, and an output 5. The input 2 receives a signal 6 representing a present electric activity of a living heart 7. The signal evaluation device 3 receives the signal 6 from the input 2 and determines a frequency spectrum 8 of the signal 6. Further, the signal evaluation device 3 determines from the frequency spectrum 8 whether the present electric activity of the heart 7 is an arrhythmia. In that case, the signal evaluation device 3 issues a trigger signal 9 triggering the pulse generator 4. Based on the frequency spectrum 8, the triggered pulse generator 4 generates a sequence 10 of electric pulses which can be applied via the output 5 to the heart 7 in order to terminate the arrhythmia. The electric pulses of the sequence 10 generated by the pulse generator 4 have a pulse repetition frequency decreasing over the sequence 10.

Figure 2:
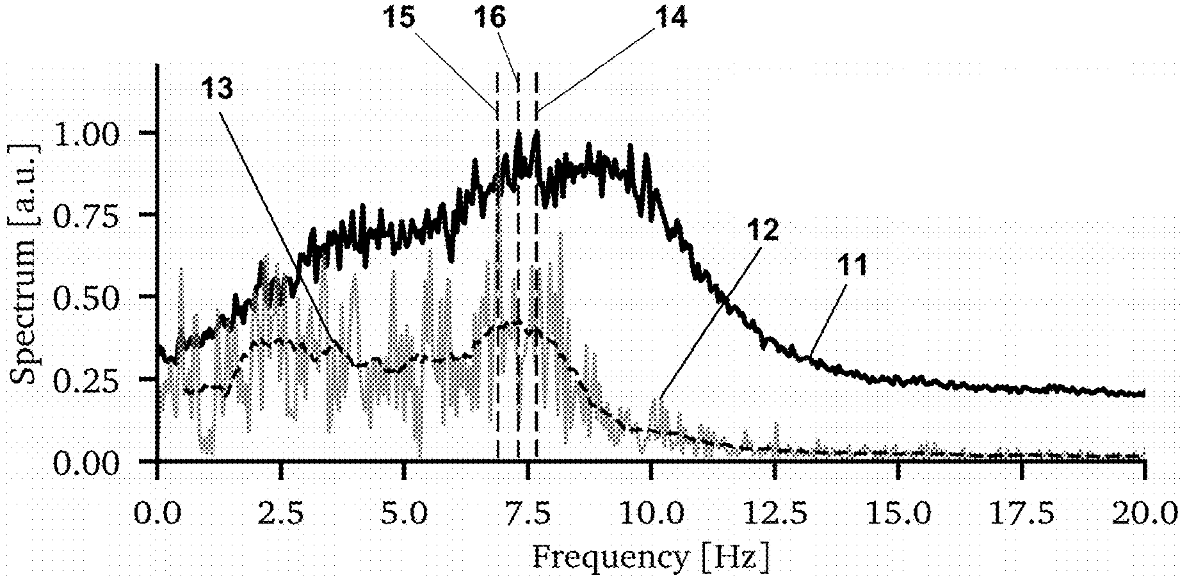
FIG. 2 shows examples of frequency spectra determined by an evaluation unit of the apparatus according to FIG. 1 in case of a ventricular fibrillation (VF) of a Fenton-Karma (FK) heart model.

FIG. 2 shows three different frequency spectra 11 to 13 of different signals 6 representing the present electric activity of the living heart as practical examples of the frequency spectrum 8 according to FIG. 1. All these frequency spectra 11 to 13 are amplitude frequency spectra. The frequency spectrum 11 is determined as follows: The present membrane voltage of each individual pixel of a spatial domain of the heart 7 is Fourier-transformed into a Fourier-spectrum. The different Fourier-spectra for the individual pixels are averaged. The frequency spectrum 12 is determined by first spatially averaging the membrane voltages of the individual pixels to calculate a pseudo-electrocardiogram (pECG) which is then Fourier-transformed. Thus, the frequency spectrum 12 corresponds to a frequency spectrum of an ECG-signal from the heart 7.

The frequency spectrum 13 is determined by smoothing the strongly fluctuating frequency spectrum 12. Although all three frequency spectra 11 to 13 represent the same electric activity of the heart 7 which clearly is an arrhythmia, i.e. a ventricular fibrillation (VT), none of the three frequency spectra clearly displays a dominant frequency. Further, peak frequencies 14 to 16 of the three frequency spectra 11 to 13 vary by +/−5%.

The sequence 10 of the electric pulses generated by the pulse generator 4 scans a main part of the frequency spectrum of the signal 6 with its decreasing pulse repetition frequency.

Figure 3:
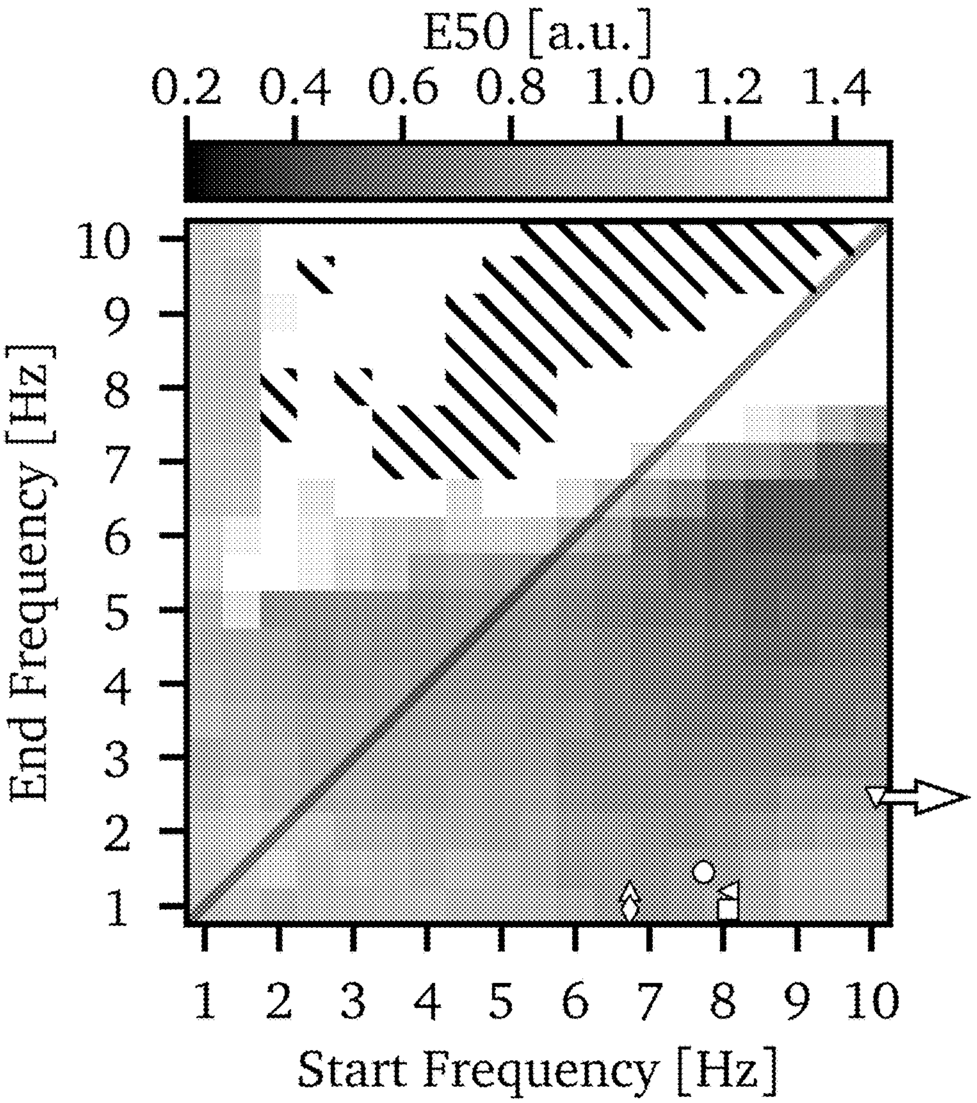
FIG. 3 is a graph indicating electric energies required to terminate the ventricular fibrillation (VF) according to FIG. 2 in the Fenton-Karma (FK) heart model with sequences of five electric pulses whose pulse repetition frequency was varied linearly between the start frequency and the end frequency indicated at a minimum success rate of 50%, i.e. E50 values, in grey shades.

FIG. 3 is a graph indicating electric pulse energies of sequences 10 of five electric pulses which are required to terminate the arrhythmia of a model of the heart 7 in computer simulations at a minimum probability of 50% (E50 values) in arbitrary units as gray shades. The heart 7 was modelled according to Fenton, F. & Karma, A. Vortex dynamics in three-dimensional continuous myocardium with fiber rotation: Filament instability and fibrillation. Chaos: 8, 20-47, DOI: 10.1063/1.166311 (1998). The brighter the gray shade in the graph the higher the electric pulse energy required for terminating the arrhythmia. Hatched areas in the graph indicate that the arrhythmia could not be terminated at the minimum probability of 50% with electric pulses of any suitable energy. The E50 values are plotted over the start frequency, i.e. the start value of the pulse repetition frequency, and the end frequency, i.e. the end value of the pulse repetition frequency, of the electric pulses of the respective sequence. Along a diagonal black line, the start frequency and the end frequency are equal. In the upper triangle of the graph, the end frequency is higher than the start frequency, and, in the lower triangle of the graph, the start frequency is higher than the end frequency which is a feature of the present disclosure. The dark area to the right with higher start frequencies in the range of 7 Hz to 10 Hz and end frequencies in the range of 3 Hz to 6 Hz indicates comparatively low E50 values, i.e. sequences 10 of the electric pulses terminating the arrhythmia at a low electric pulse energy.

Figure 4:
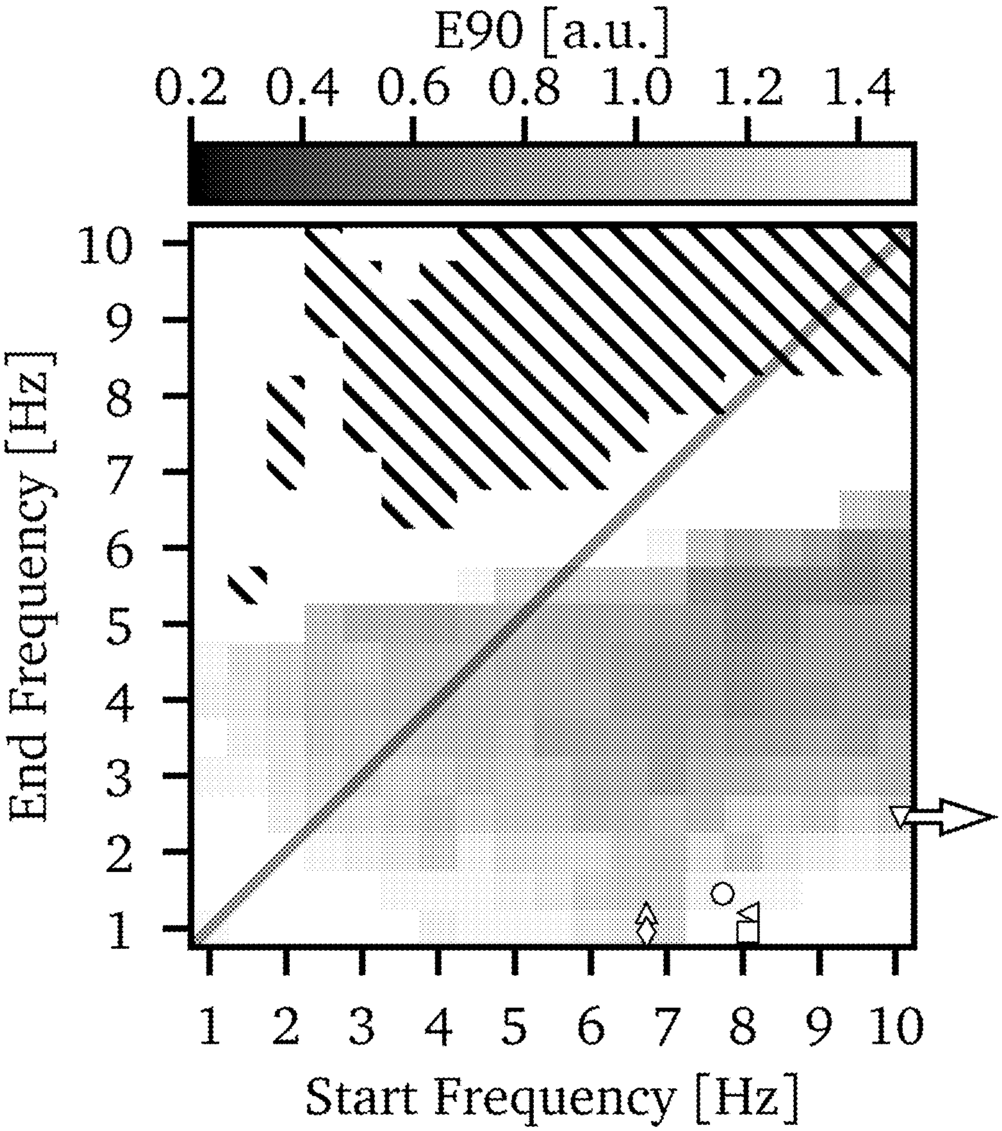
FIG. 4 is a graph similar to FIG. 3 also relating to sequences of five electric pulses, but indicating electric energies required to terminate the ventricular fibrillation (VF) at a minimum success rate of 90%, i.e. E90 values, in grey shades.

FIG. 4 is a graph indicating the electric pulse energy of the electric pulses of the sequences of five electric pulses required for terminating the arrhythmia of the Fenton-Karma (FK) model of the heart 7 at a probability of 90%. As expected, the gray shades, in general, indicate higher electric pulse energies, and the hatched areas in the graph are larger. The area of particularly low E90 values concentrates at starting frequencies between 7 Hz and 10 Hz and end frequencies between 3 Hz and 6 Hz.

Figure 5:
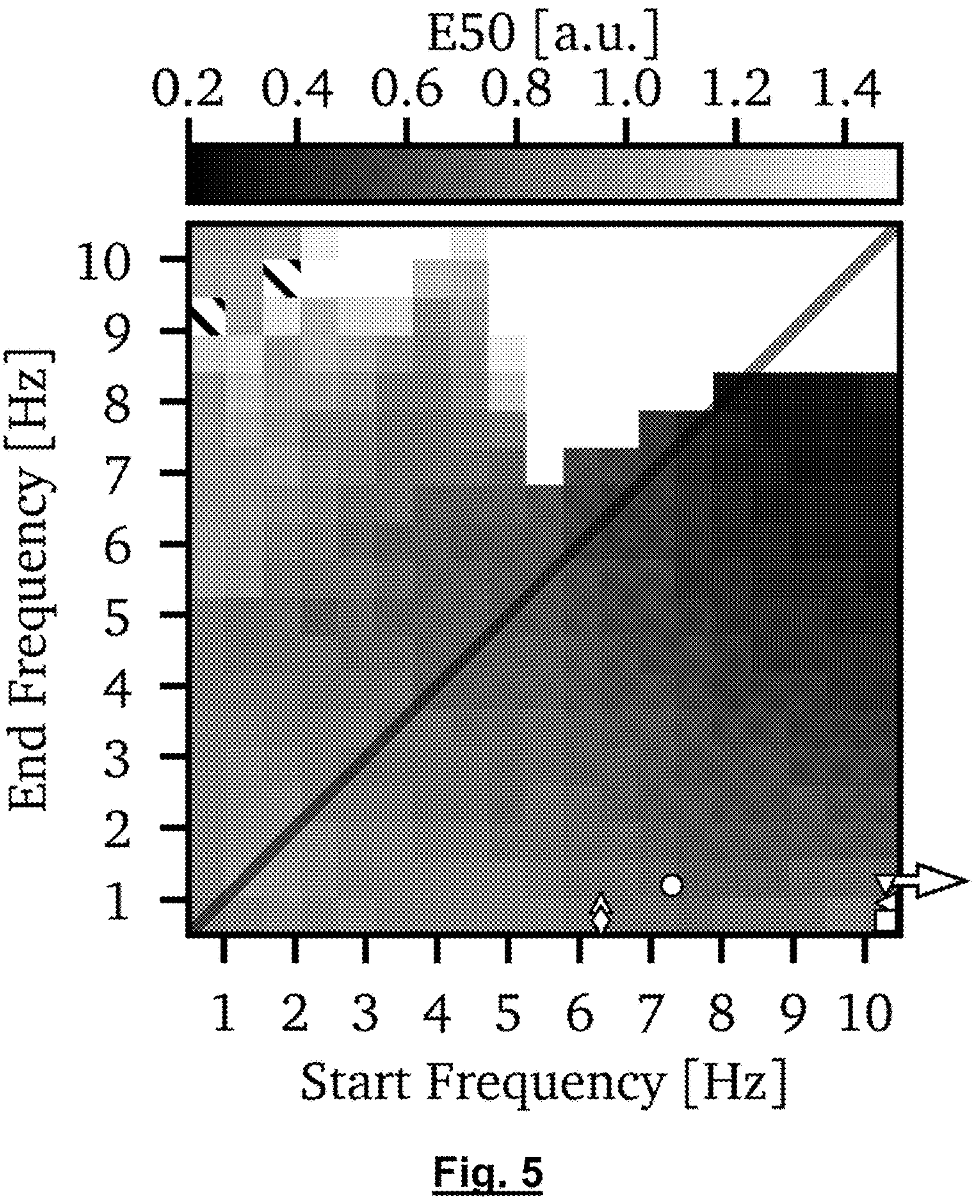
FIG. 5 is a graph corresponding to FIG. 3, but relating to sequences of ten electric pulses.
Figure 6:
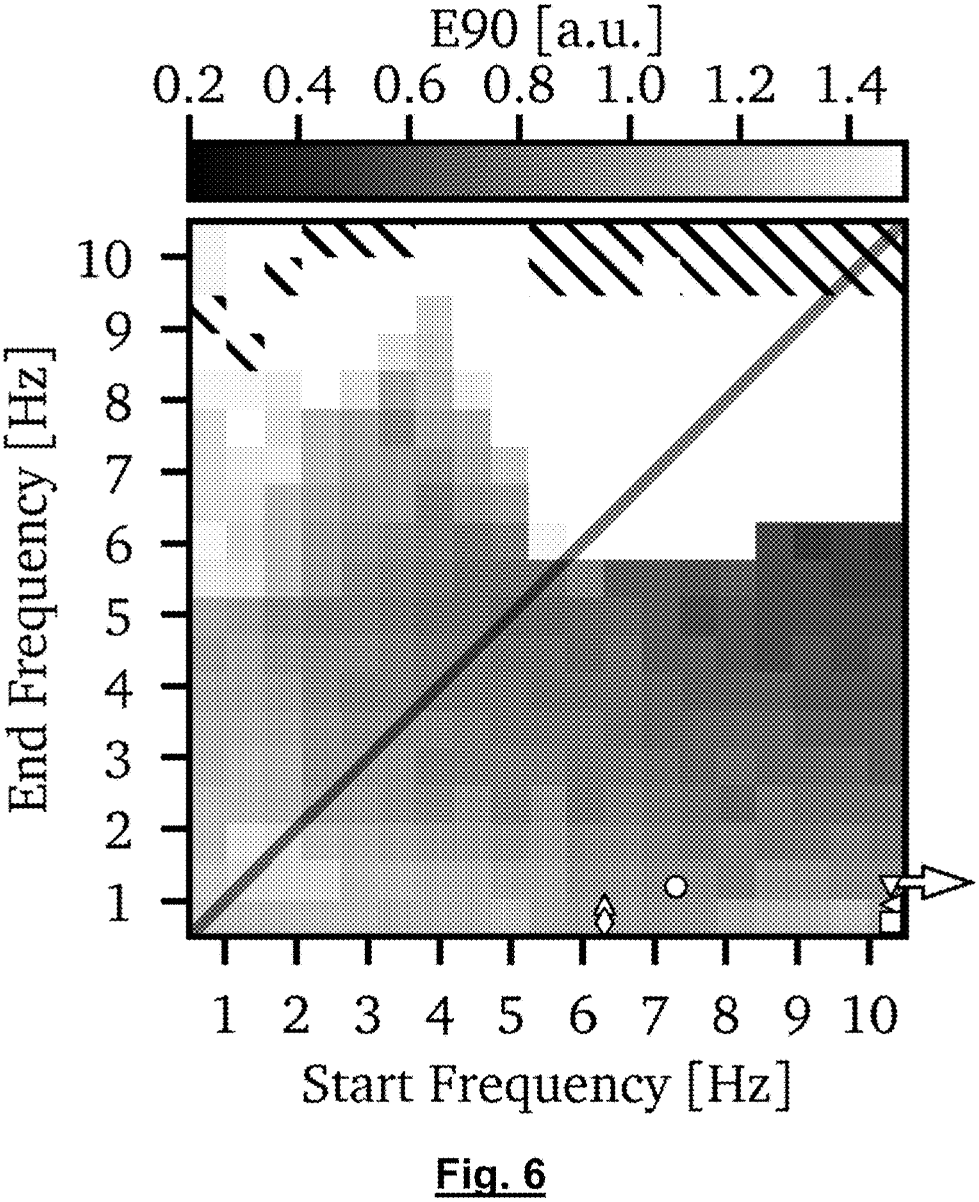
FIG. 6 is a graph corresponding to FIG. 4, but, like FIG. 5, relating to sequences of ten electric pulses.

FIGS. 5 and 6 correspond to FIGS. 3 and 4 except of that the number of pulses of the sequence 10 is ten instead of five. Here, the hatched areas are reduced in size as compared to FIGS. 3 and 5, respectively. Further, a very interesting fact appears from a comparison of FIGS. 5 and 6. Whereas the darkest area in FIG. 5 concentrates at starting frequencies between 8 Hz and 10 Hz and end frequencies between 7 Hz and 8 Hz, i.e. at a quite low difference between the start and end frequencies, the darkest area in FIG. 6 concentrates at clearly lower end frequencies. This means that a high termination probability requires a higher decrease in the pulse repetition frequency over the sequence 10 of electric pulses.

Figure 7:
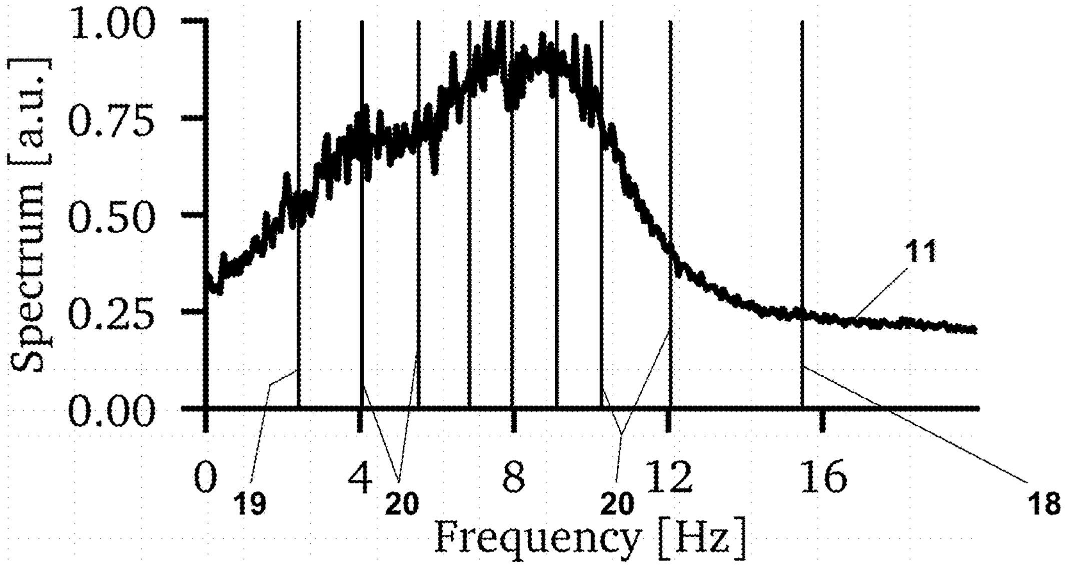
FIG. 7 illustrates one of the frequency spectra of FIG. 1 whose integral is divided into eight equal parts by a start value, an end value and seven intermediate values of a pulse repetition frequency.
Figure 8:
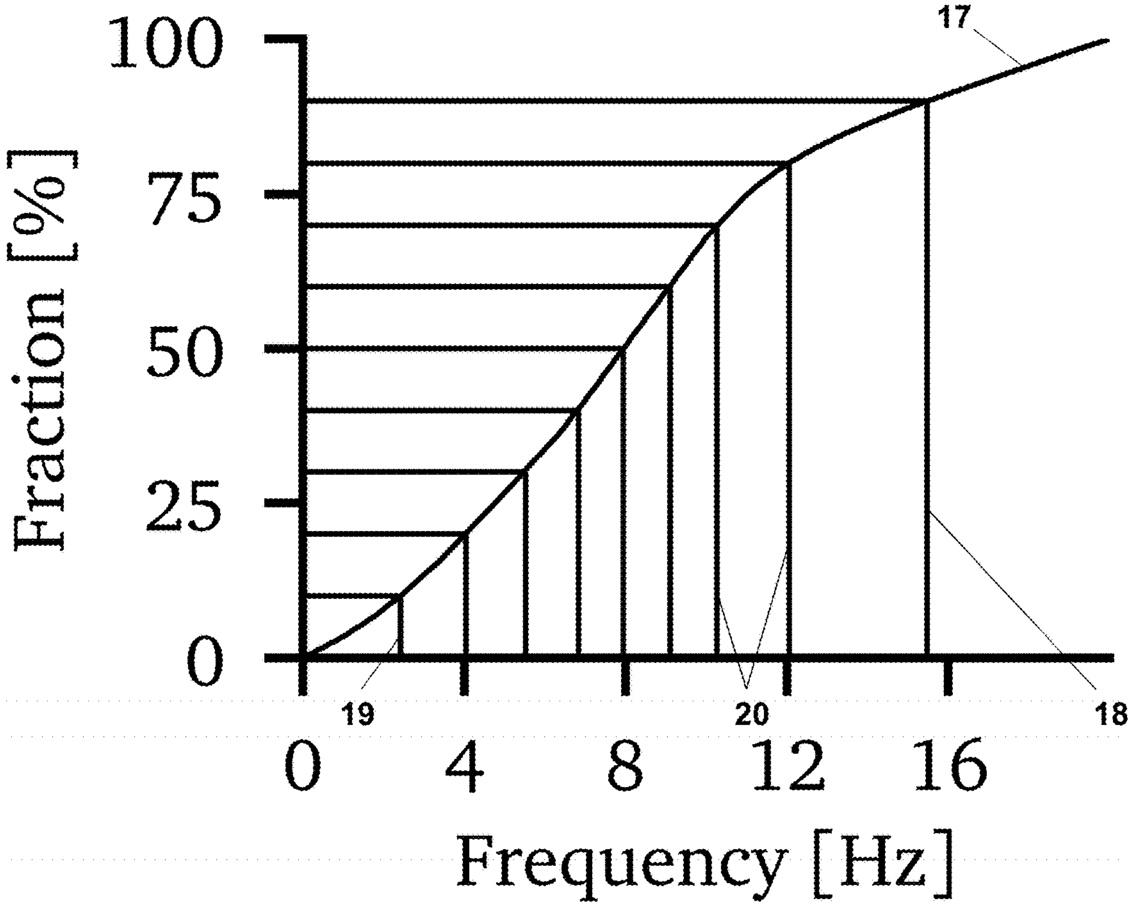
FIG. 8 shows the course of the integral of the frequency spectrum according to FIG. 7 over the nine values of the pulse repetition frequency according to FIG. 7.

FIGS. 7 to 8 illustrate the concept of setting the values of the pulse repetition frequency of the sequence depending on an integral of the frequency spectrum 11. FIG. 7 shows the same frequency spectrum 11 as FIG. 1, and FIG. 8 shows the integral 17 of the frequency spectrum 11, i.e. the area under the frequency spectrum 11, increasing from 0 at a frequency of 0 Hz. The integral 17 is calculated up to a frequency of 20 Hz. By nine values 18-20 of the pulse repetition frequency indicated in FIGS. 7 and 8, the integral 17 according to FIG. 8 is subdivided into ten equal parts, each part of the integral 17 corresponding to a fraction of 10% of the full integral over the frequency range from 0 Hz to 20 Hz. The values include a start value 18 corresponding to the start frequency indicated in FIGS. 3 to 6, an end value 19 corresponding to the end frequency according to FIGS. 3 to 6, and intermediate values 20 which are not arranged at equal distances in frequency, but at a higher density in those areas, in which the frequency spectrum displays higher values indicating a higher electric activity of the heart 7 at the respective frequencies.

Figure 9:
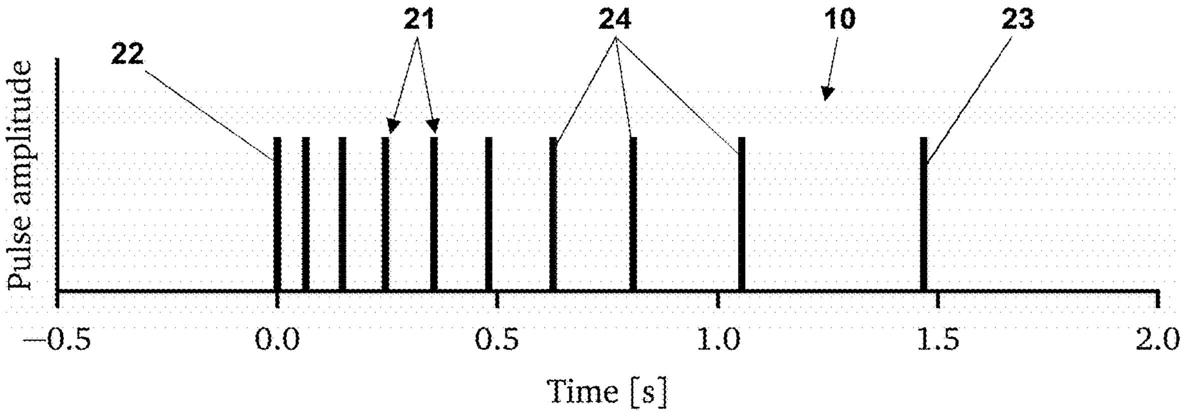
FIG. 9 shows a sequence of electric pulses generated at nine values of the pulse repetition frequency according to FIGS. 7 and 8.

FIG. 9 shows the resulting sequence 10 of electric pulses 21 beginning with a start pulse 22, ending with an end pulse 23 and including eight intermediate pulses 14. The intervals or distances in time between the pulses 21 increase with time and this increase is also not linear but reflects the shape of the frequency spectrum 11.

In a same way as illustrated by FIGS. 7 to 9, the pulse repetition frequencies of the sequences 10 of ten electric pulses 21 can also be set based on the other two frequency spectra 12 and 13 depicted in FIG. 1 or based on any other frequency spectrum of a signal representing the present electric activity of the heart 7. Further, it is not necessary to make use of the respective frequency spectrum up to the frequency of 20 Hz. Instead, another cut-off value may be used, like for example 10 Hz, particularly when using the spectra 12 and 13 of FIG. 2 which are already nearly down to 0 at the frequency of 10 Hz. Further, the principle explained with reference to FIGS. 7 to 9 may also be used for setting the pulse repetition frequency for a sequence of any other number of electric pulses 21, like for example, five electric pulses 21.

Figure 10:
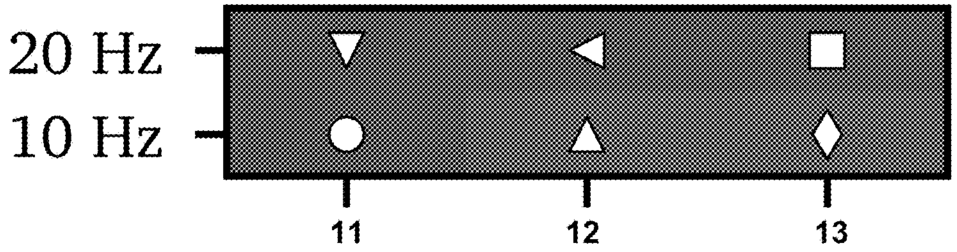
FIG. 10 is a graph indicating electric energies required to terminate the ventricular fibrillation (VF) according to FIG. 2 in the Fenton-Karma (FK) heart model with sequences of five electric pulses at a minimum success rate of 50%, i.e. E50 values, in grey shades. Here, the pulse repetition frequencies have been set according to FIGS. 7 to 9 for the three different spectra according to FIG. 1 applying a cut-off frequency of 10 Hz and 20 Hz, respectively. Identical black-rimmed white graphic symbols in FIGS. 10 and 3 indicate sequences of same start and end frequencies.
Figure 11:
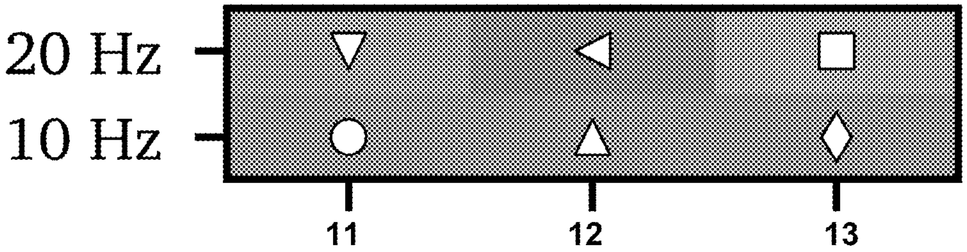
FIG. 11 is a graph similar to FIG. 10 also relating to sequences of five electric pulses, but indicating electric energies required to terminate the ventricular fibrillation (VF) at a minimum success rate of 90%, i.e. E90 values, in grey shades. Identical black-rimmed white graphic symbols in FIGS. 11 and 4 indicate sequences of same start and end frequencies.
Figure 12:
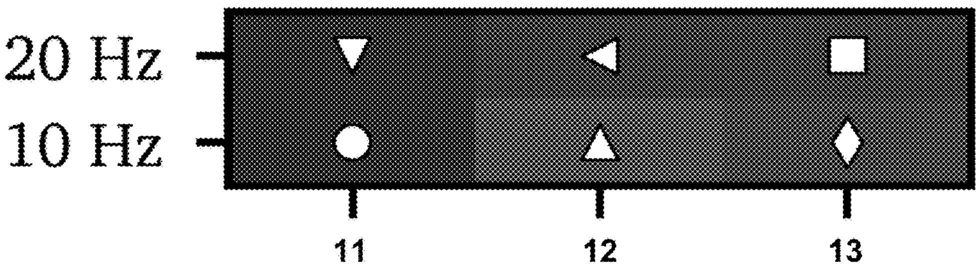
FIG. 12 is a graph corresponding to FIG. 10, but relating to sequences of ten electric pulses as depicted in FIG. 9. Identical black-rimmed white graphic symbols in FIGS. 12 and 4 indicate sequences of same start and end frequencies.
Figure 13:
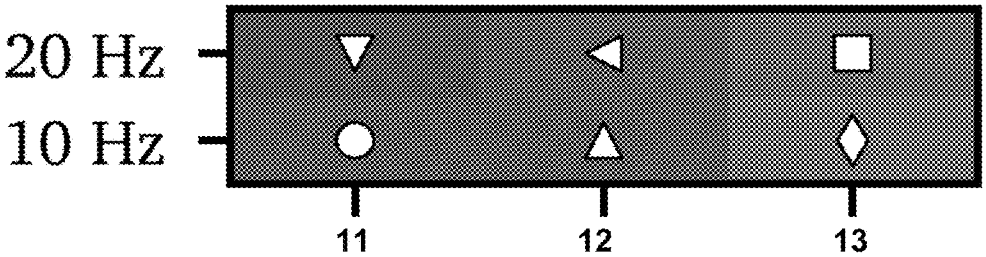
FIG. 13 is a graph corresponding to FIG. 11, but, like FIG. 12, relating to sequences of ten electric pulses. Identical black-rimmed white graphic symbols in FIGS. 13 and 5 indicate sequences of same start and end frequencies.

For sequences of five pulses in FIGS. 10 and 11 and ten pulses in FIGS. 12 and 13, E50 values in FIGS. 10 and 12 and E90 values in FIGS. 11 and 13 are indicated by the same gray shades as in FIGS. 3 to 6. Separate E50 and E90 values are depicted for the three frequency spectra 11 to 13 according to FIG. 2 and for two different cut-off frequencies of 10 Hz and 20 Hz. Further, black-rimmed white graphic symbols which are indicated in FIGS. 10 to 13 refer to black-rimmed white graphic symbols in FIGS. 3 to 6. Same black-rimmed white graphic symbols in FIGS. 3 and 10, FIGS. 4 and 11, FIGS. 5 and 12, and FIGS. 6 and 14, respectively, point to sequences having same start and end frequencies. The arrows which are attached to the downwardly-pointing triangles in FIGS. 5 and 6 and point to the right indicate that the respective sequence is outside the start frequency range depicted. Although the black-rimmed white graphic symbols in FIGS. 3 to 6 do not appear in the darkest areas of these Figures, all gray shades depicted in FIGS. 10 to 13 are about equal to the gray shades in the darkest areas of FIGS. 3 to 6. This means that, independent on the frequency spectrum 11 to 13 actually used and independent on the cut-off frequency for the integral 17 actually implemented, an optimum or close to optimum sequence 10 of electric pulses 21 is found by setting the pulse repetition frequencies according to FIGS. 7 to 9, i.e. without extensive search for an optimum combination of start and end frequencies. Such an extensive search is not possible in the practical use of an apparatus for terminating an arrhythmia of a living heart. Thus, setting the pulse repetition frequency according to FIGS. 7 to 9 which can be implemented fully automatically and in or close to real time will be an advantage. In practical use, the apparatus 1 of FIG. 1 implementing the concept according to FIGS. 7 to 9 will generate a sequence of electric pulses of rather low electric pulse energy, but nevertheless achieve a high success rate in terminating an arrhythmia of any living heart 7 from which any signal 6 representing its electrical activity is available and to which the sequence 10 of the low energy electric pulses will be applied.

Figure 14:
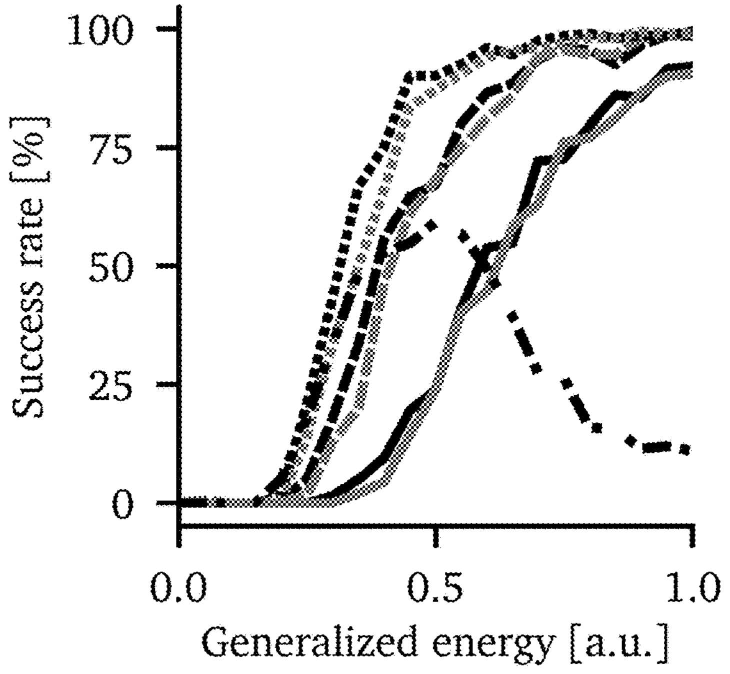
FIG. 14 shows dose-response curves for different pulse numbers for terminating the ventricular fibrillation in the Fenton-Karma (FK) heart model, the pulse repetition frequencies being set according to FIGS. 7 to 9 based on one of the frequency spectra of FIG. 1 applying a cut-off frequency of 10 Hz.
Figure 15:
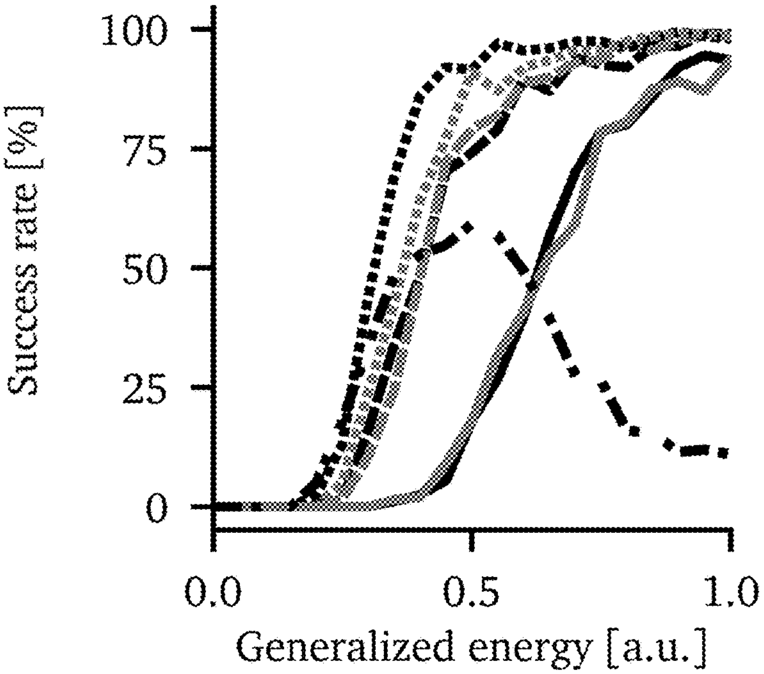
FIG. 15 shows similar dose-response curves as FIG. 14 but applying a cut-off frequency of 20 Hz.

The dose-response curves depicted in FIGS. 14 and 15 are coded as follows. The continuous black lines are dose-response curves for five pulses generated according to FIGS. 7 to 19 based on the spectrum 13 according to FIG. 2, i.e. based on an amplitude spectrum. The continuous grey lines depict corresponding dose-response curves in case of five pulses set according to FIGS. 7 to 9 based on a pulse frequency spectrum or pulse spectral density (PSD) corresponding to the amplitude frequency spectrum 13 of FIG. 2. The dose-response curves depicted with dashed lines are those for 10 pulses and the dose-response curves depicted with dotted lines are those for 15 pulses whose pulse repetition frequency has been set according to FIGS. 7 to 9. The dose-response curve depicted with a dash-dotted line relates to a comparison example achieved with 10 equidistant pulses. FIGS. 14 and 15 show that setting the pulse repetition frequencies according to FIGS. 7 to 9 may result in an advantage over equidistant pulses. Further, the success rate strongly increases from 5 to 10 pulses and further less strongly increases from 10 to 15 pulses. The differences between the dose-response curves for pulses whose pulse repetition frequency have been determined based on the amplitude or power frequency spectra do not differ much but there still is an advantage for the amplitude frequency spectrum base. The higher cut-off frequency of FIG. 15 results in a slightly steeper increase of the success rate over the generalized energy which is indicated as the energy per pulse.

Figure 16:
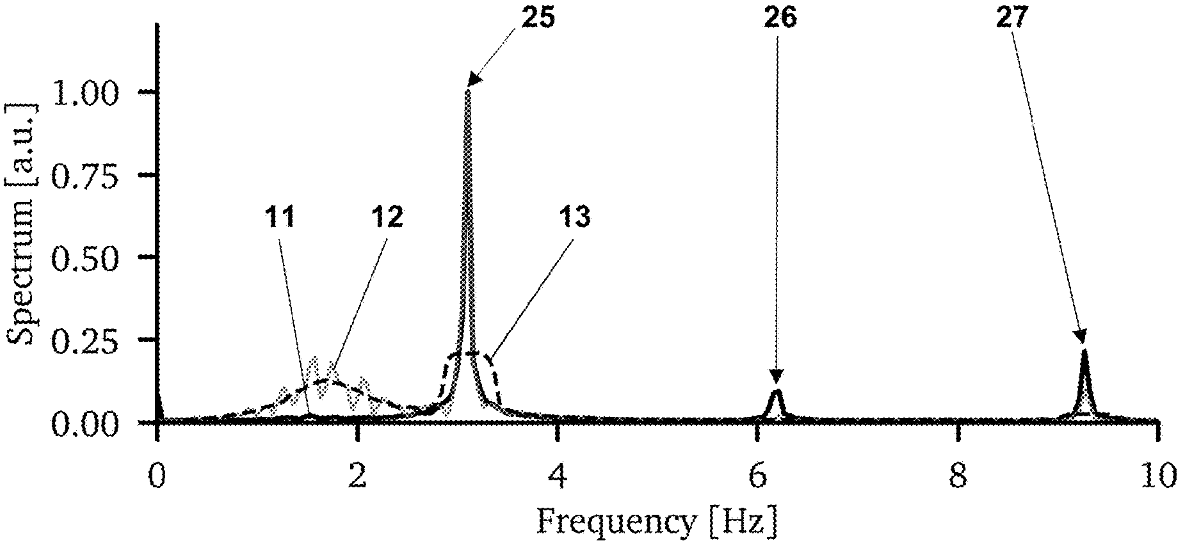
FIG. 16 shows examples of frequency spectra determined by the evaluation unit of the apparatus according to FIG. 1 in case of a ventricular tachycardia (VT) of the Fenton-Karma (FK) heart model.
Figure 17:
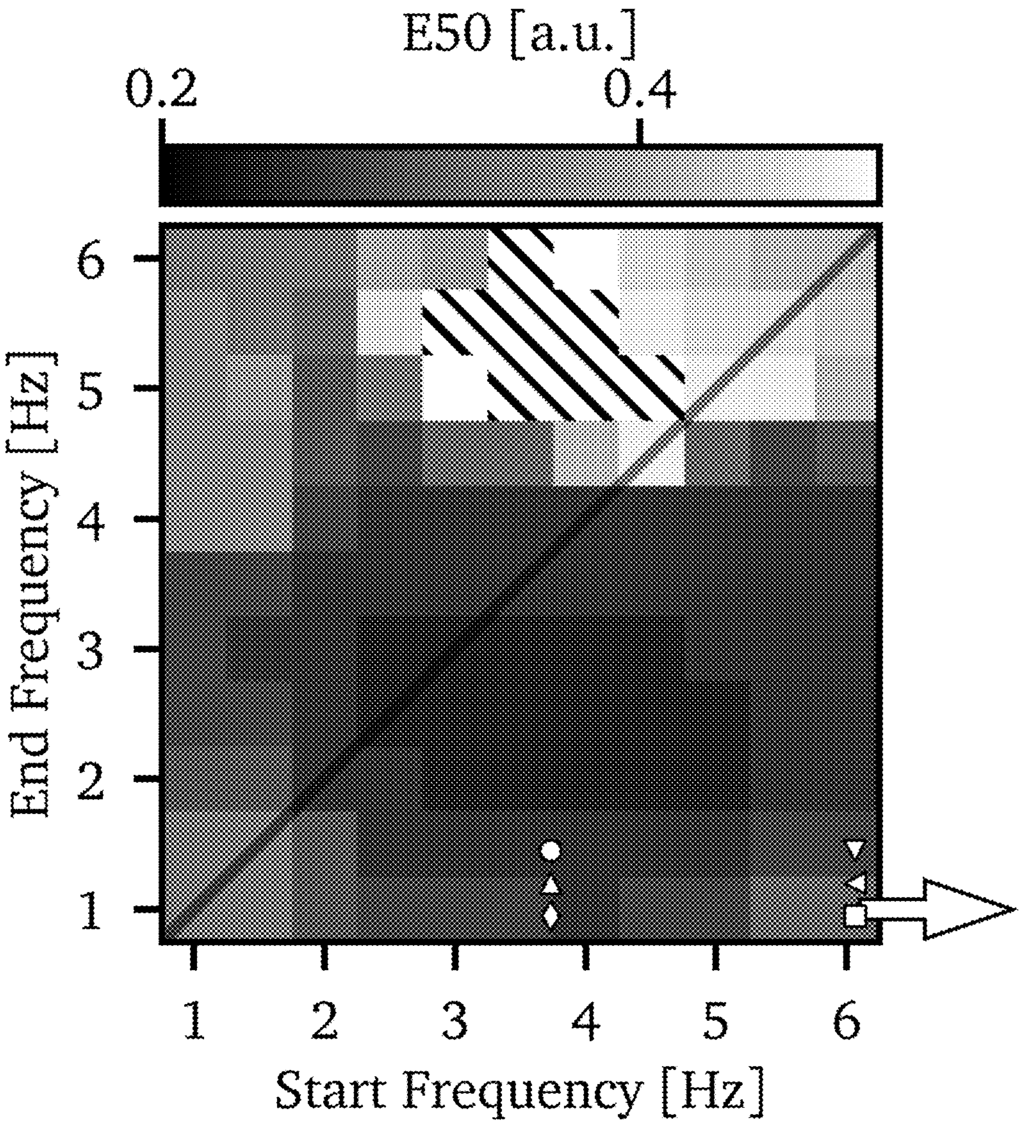
FIGS. 17, 18, 19 and 20 correspond to FIGS. 3 to 6 but are graphs indicating electric energies required to terminate the ventricular tachycardia (VT) according to FIG. 16 in the Fenton-Karma (FK) heart model.
Figure 21:
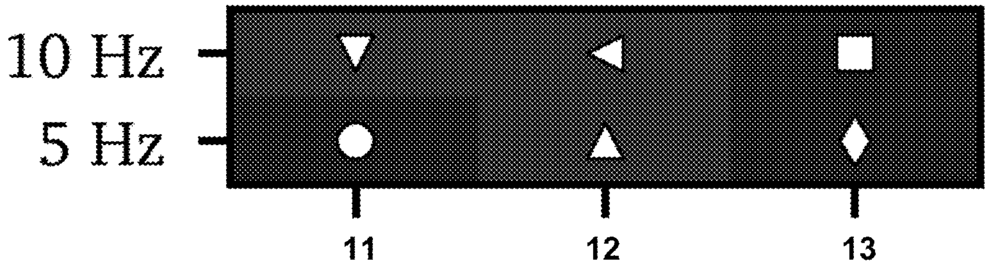
FIGS. 21, 22, 23 and 24 correspond to FIGS. 10 to 13 but are graphs indicating electric energies required to terminate the ventricular tachycardia (VT) according to FIG. 16 in the Fenton-Karma (FK) heart model, the pulse repetition frequencies being set according to FIGS. 7 to 9 based on one of the frequency spectra of FIG. 16 applying cut-off frequencies of 5 Hz and 10 Hz.
Figure 18:
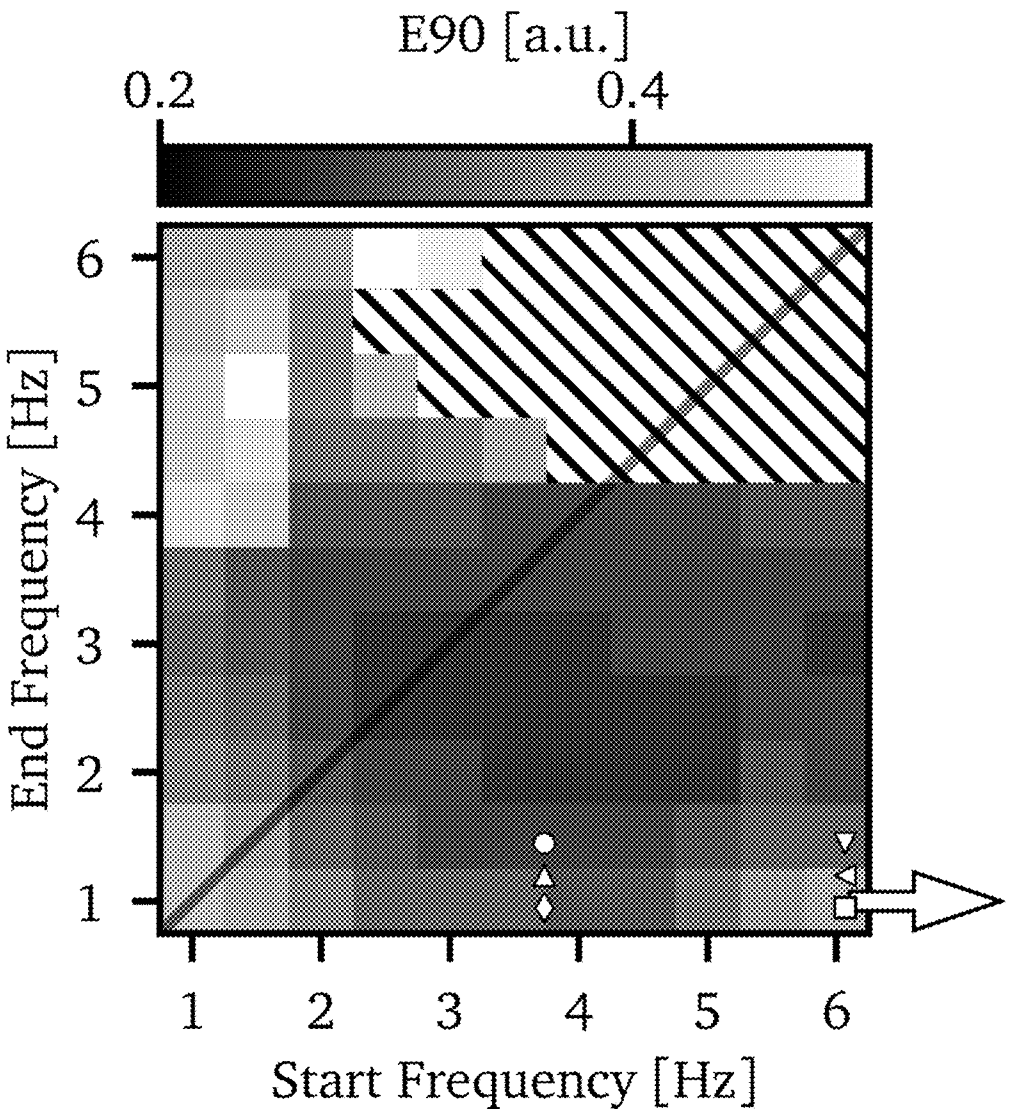
Figure 22:
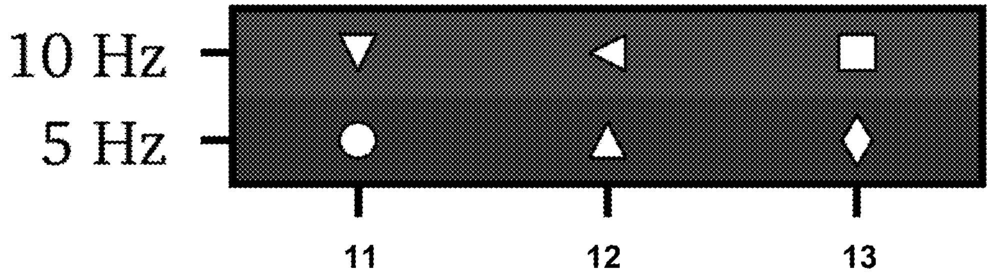
Figure 19:
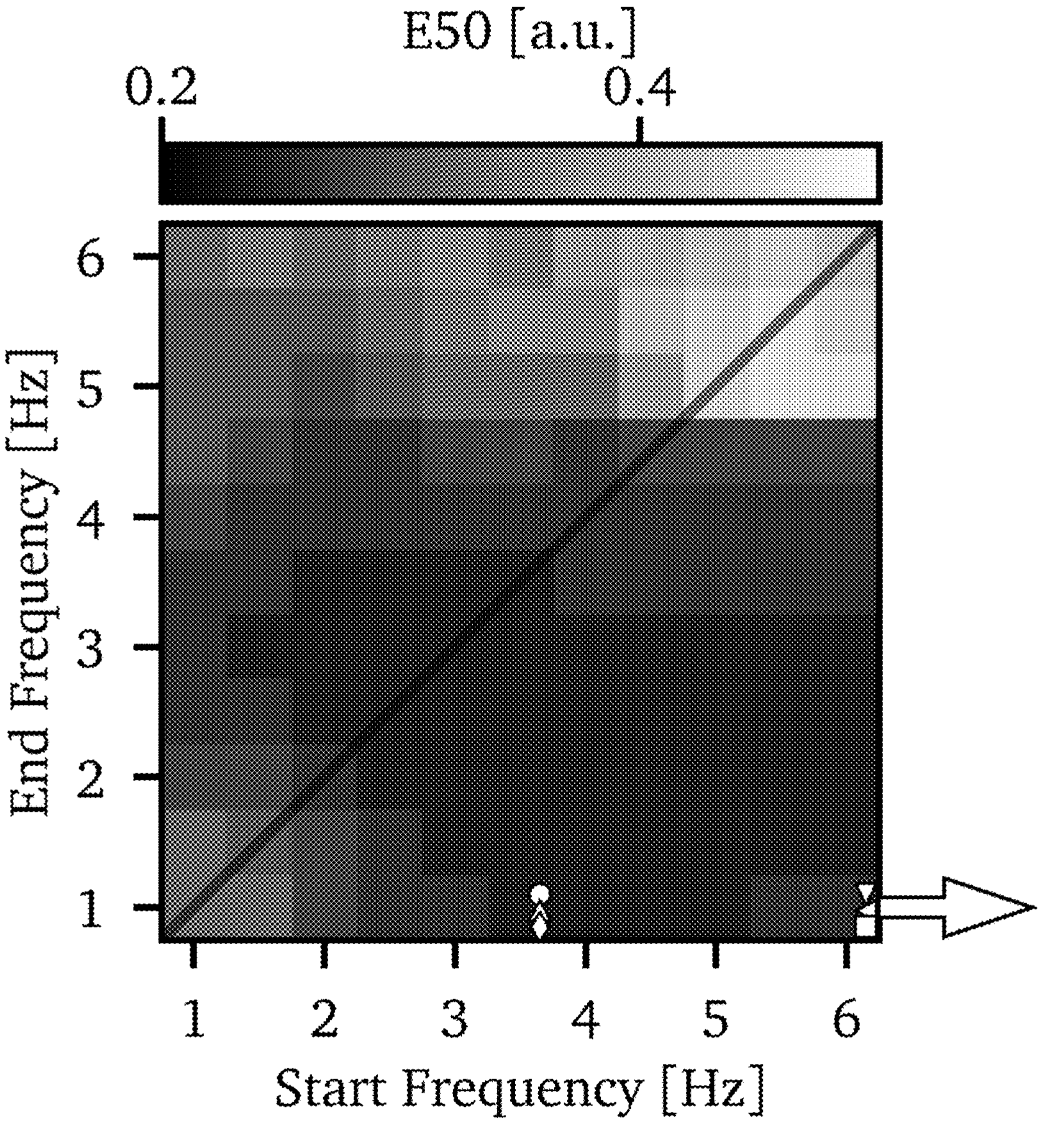
Figure 23:
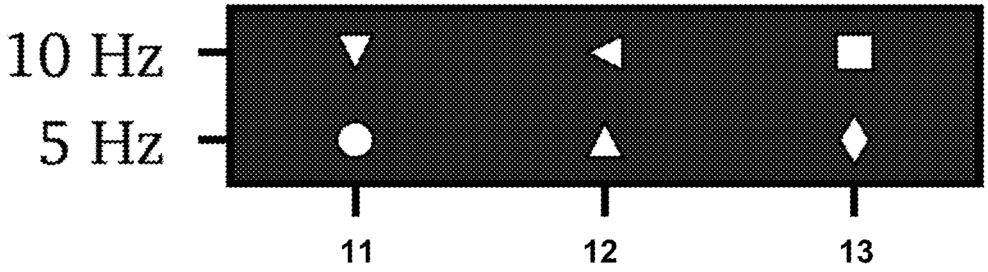
Figure 20:
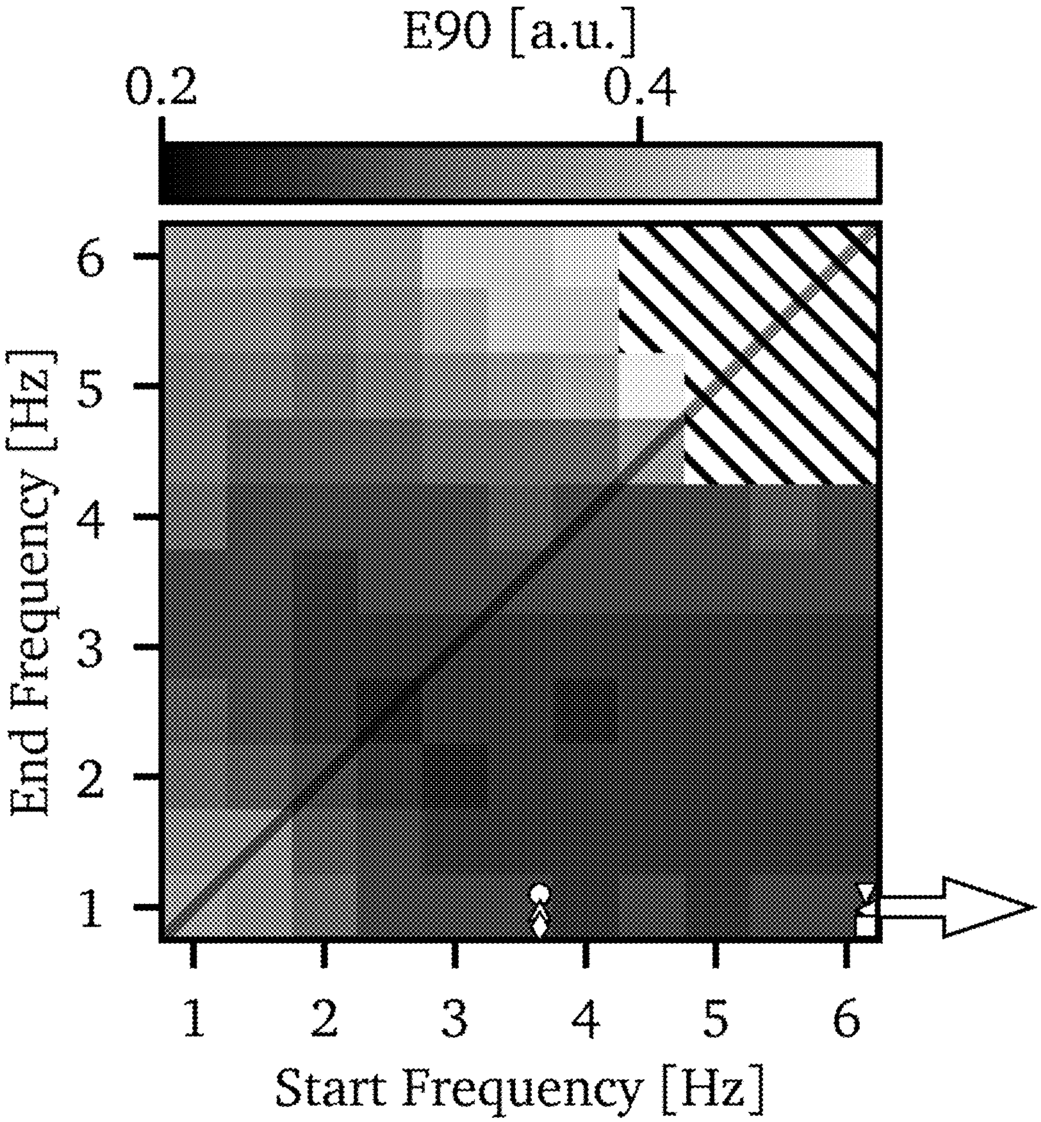
Figure 24:
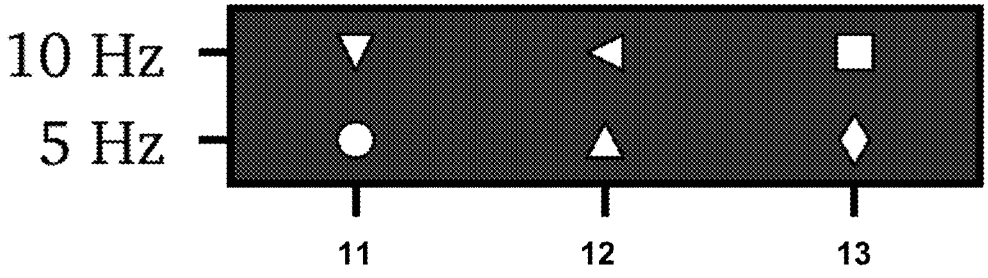

FIG. 16 shows examples of frequency spectra 11 to 13 in case of a ventricular tachycardia (VT) of the Fenton-Karma (FK) heart model. The spectra have been determined in the same way as described with reference to FIG. 2. All the frequency spectra are amplitude frequency spectra and show peaks at a dominant frequency 25 of the VT and at a first harmonic 26 and a second harmonic 27 of the dominant frequency 25. In the determination of the pulse repetition frequency of pulses for terminating the VT according to FIGS. 7 to 9, the cut-off frequency for the integral 17 may be set to a smaller value of, for example, 10 Hz or 5 Hz, the latter cut-off frequency excluding both harmonics 26 and 27.

FIGS. 17 to 24 show that, also in terminating the ventricular tachycardia (VT) according to FIG. 16, the determination of the pulse repetition frequency according to FIGS. 7 to 9 results in success rates, see FIGS. 21 to 24, which are essentially similar to the best success rates in the full range of start and end frequencies depicted in FIGS. 17 to 20. Thus, the apparatus according to the present disclosure is both suited for terminating fibrillation and tachycardia.

Many variations and modifications may be made to the preferred embodiments of the invention without departing substantially from the spirit and principles of the invention. All such modifications and variations are intended to be included herein within the scope of the present invention, as defined by the following claims.

We claim:

1. An apparatus for terminating an arrhythmia of a living heart, the apparatus comprising:

a signal evaluation device configured for receiving a signal representing a present electric activity of the living heart, and for determining a frequency spectrum of the signal; and a pulse generator configured for generating a sequence of electric pulses to be applied to the living heart at a pulse repetition frequency that depends of the frequency spectrum in such a way that the pulse repetition frequency of the electric pulses decreases by at least 20% over the sequence.

2. The apparatus of claim 1, wherein the pulse generator is configured for generating the sequence of the electric pulses such that the pulse repetition frequency decreases at least one of monotonically and strictly monotonically.

3. The apparatus of claim 1, wherein the pulse generator is configured for generating the sequence of the electric pulses such that the pulse repetition frequency of the electric pulses decreases by at least 30% over the sequence.

4. The apparatus of claim 1, wherein the pulse generator is configured for generating the sequence of the electric pulses such that the pulse repetition frequency of the electric pulses decreases by at least 50% over the sequence.

5. The apparatus of claim 3, wherein the pulse generator is configured for generating the sequence of the electric pulses such that the pulse repetition frequency of the electric pulses decreases by up to 80% over the sequence.

6. The apparatus of claim 1, wherein the pulse generator is configured for generating the sequence of the electric pulses such that the sequence consists of at least 3 electric pulses and of not more than 20 electric pulses.

7. The apparatus of claim 1, wherein the pulse generator is configured for generating the sequence of the electric pulses such that an integral of a high frequency part of the frequency spectrum, the high frequency part of the frequency spectrum extending down to a start value of the pulse repetition frequency of the electric pulses of the sequence, is at least 5% and not more than 20% of a full integral of the frequency spectrum.

8. The apparatus of claim 1, wherein the pulse generator is configured for generating the sequence of the electric pulses such that a start value of the pulse repetition frequency of the electric pulses of the sequence is at least 5 Hz and not more than 15 Hz.

9. The apparatus of claim 7, wherein the pulse generator is configured for generating the sequence of the electric pulses such that an integral of a low frequency part of the frequency spectrum, the low frequency part of the frequency spectrum extending up to an end value of the pulse repetition frequency of the electric pulses of the sequence, is at least 5% and not more than 20% of the full integral the frequency spectrum.

10. The apparatus of claim 8, wherein the pulse generator is configured for generating the sequence of the electric pulses such that an end value of the pulse repetition frequency of the electric pulses of the sequence is at least 0.5 Hz and not more than 4 Hz.

11. The apparatus of claim 1, wherein the pulse generator is configured for generating the sequence of the electric pulses such that intermediate values of the pulse repetition frequency of the electric pulses of the sequence are arranged such as to divide a full integral of the frequency spectrum into essentially equal parts.

12. The apparatus of claim 1, wherein the signal evaluation device is configured for receiving an electrocardiogram (ECG) signal as the signal representing the electric activity of the living heart, and for determining a frequency spectrum of the ECG signal.

13. The apparatus of claim 1, wherein the signal evaluation device is configured for Fourier-transforming the signal representing the electric activity of the living heart in determining the frequency spectrum of the signal.

14. The apparatus of claim 1, wherein the signal evaluation device is configured for smoothing a preliminary frequency spectrum of the signal in determining the frequency spectrum of the signal on which the pulse repetition frequency of the electric pulses is depending.

15. The apparatus of claim 1, wherein the pulse generator is configured for generating the sequence of the electric pulses such that the sequence consists of pulses of equal voltage and energy.

16. An apparatus for terminating an arrhythmia of a living heart, the apparatus comprising:

a signal evaluation device comprising stored evaluation instructions and, when executing the stored evaluation instructions, being configured for receiving a signal representing a present activity of the living heart, and for determining a frequency spectrum of the signal; and a pulse generator comprising stored generation instructions and, when executing the stored generation instructions, being configured for generating a sequency of electric pulses to be applied to the living heart at a variable pulse repetition frequency of the electric pulses decreases by at least 20% over the sequency.

17. The apparatus of claim 16, wherein the pulse generator, when executing the stored generation instructions, is configured for generating the sequence of the electric pulses such that the variable pulse repetition frequency decreases strictly monotonically;

the variable pulse repetition frequency of the electric pulses decreases by at least 50% over the sequence and by up to 70% over the sequence; and the sequence consists of at least 4 electric pulses and of not more than 15 electric pulses.

18. The apparatus of claim 17, wherein the pulse generator, when executing the stored generation instructions, is configured for generating the sequence of the electric pulses such that an integral of a high frequency part of the frequency spectrum, the high frequency part of the frequency spectrum extending down to a start value of the variable pulse repetition frequency of the electric pulses of the sequence, is at least 8% and not more than 15% of a full integral of the frequency spectrum; and an integral of a low frequency part of the frequency spectrum, the low frequency part of the frequency spectrum extending up to an end value of the variable pulse repetition frequency of the electric pulses of the sequence, is at least 8% and not more than 15% of the full integral the frequency spectrum.

19. The apparatus of claim 18, wherein the pulse generator, when executing the stored generation instructions, is configured for generating the sequence of the electric pulses such that the start value of the variable pulse repetition frequency of the electric pulses of the sequence is at least 8 Hz and not more than 10 Hz; and the end value of the variable pulse repetition frequency of the electric pulses of the sequence is at least 1 Hz and not more than 2 Hz.

20. The apparatus of claim 19, wherein the pulse generator, when executing the stored generation instructions, is configured for generating the sequence of the electric pulses such that intermediate values of the variable pulse repetition frequency of the electric pulses of the sequence are arranged such as to divide the full integral of the frequency spectrum into essentially equal parts.

* * * * *